US010321978B2

(12) United States Patent
Orikasa et al.

(10) Patent No.: US 10,321,978 B2
(45) Date of Patent: *Jun. 18, 2019

(54) ORTHODONTIC BRACKET

(71) Applicant: TOMY INCORPORATED, Futaba-gun, Fukushima (JP)

(72) Inventors: Masaaki Orikasa, Natori (JP); Shingo Katayose, Fukushima (JP); Kosei Endo, Fukushima (JP)

(73) Assignee: TOMY INCORPORATED, Futaba-gun, Fukushima (JP)

( * ) Notice: Subject to any disclaimer, the term of this patent is extended or adjusted under 35 U.S.C. 154(b) by 5 days.

This patent is subject to a terminal disclaimer.

(21) Appl. No.: 15/883,442

(22) Filed: Jan. 30, 2018

(65) Prior Publication Data

US 2018/0153655 A1 Jun. 7, 2018

Related U.S. Application Data

(63) Continuation-in-part of application No. 13/819,797, filed as application No. PCT/JP2011/070639 on Sep. 9, 2011, now Pat. No. 9,901,423.

(30) Foreign Application Priority Data

Sep. 17, 2010 (JP) ................................ 2010-210121

(51) Int. Cl.
*A61C 7/28* (2006.01)
*A61C 7/02* (2006.01)
(52) U.S. Cl.
CPC .............. *A61C 7/287* (2013.01); *A61C 7/285* (2013.01); *A61C 7/02* (2013.01)
(58) Field of Classification Search
CPC .... A61C 7/00; A61C 7/12; A61C 7/14; A61C 7/287

(Continued)

(56) References Cited

U.S. PATENT DOCUMENTS 4,144,642 A * 3/1979 Wallshein ................ A61C 7/30
433/11
4,197,642 A * 4/1980 Wallshein ................ A61C 7/30
433/11

(Continued)

FOREIGN PATENT DOCUMENTS

DE 102004056168 B4 9/2007
JP 50-80694 A 6/1975

(Continued)

OTHER PUBLICATIONS

Advertisement of the opponent on p. 11 of No. 3 of the magazine Kieferorothopadie Nachrichten dated Mar. 2009. (1 page total).

(Continued)

*Primary Examiner* — Matthew M Nelson
(74) *Attorney, Agent, or Firm* — Sughrue Mion, PLLC

(57) ABSTRACT

An orthodontic bracket is provided. The orthodontic bracket includes a base part; a bracket body mounted on the base part and having a retaining projection provided on an upper face thereof; a clip having a U-shaped cross-section, the clip being mounted on the bracket body and including an upper part along the upper face of the bracket body, a lower part along a lower face of the bracket body, a curved part therebetween, and an engaging hole provided in the upper part of the clip in a position that corresponds to a position of the retaining projection of the bracket body such that the retaining projection projects through the engaging hole when the clip is in an open position thereon; and an archwire slot in the upper face of the bracket body that extends perpendicular to a moving direction of the clip.

6 Claims, 14 Drawing Sheets

(58) Field of Classification Search
USPC ............................................. 433/8–24
See application file for complete search history.

(56) References Cited

U.S. PATENT DOCUMENTS

| | | | | |
|---|---|---|---|---|
| 4,492,573 | A * | 1/1985 | Hanson | A61C 7/287 433/11 |
| 5,466,151 | A * | 11/1995 | Damon | A61C 7/146 433/10 |
| 5,711,666 | A * | 1/1998 | Hanson | A61C 7/145 433/11 |
| 5,906,486 | A * | 5/1999 | Hanson | A61C 7/287 433/10 |
| 5,967,773 | A * | 10/1999 | Roman | A61C 7/30 433/11 |
| 6,071,119 | A * | 6/2000 | Christoff | A61C 7/285 433/13 |
| 6,655,957 | B2 | 12/2003 | Abels et al. | |
| 7,963,768 | B2 * | 6/2011 | Hilliard | A61C 7/287 433/11 |
| 9,089,386 | B2 * | 7/2015 | Hagelganz | A61C 7/30 |
| 2002/0110772 | A1 | 8/2002 | Abels et al. | |
| 2002/0110775 | A1 * | 8/2002 | Abels | A61C 7/125 433/11 |
| 2002/0119414 | A1 * | 8/2002 | Orikasa | A61C 7/28 433/10 |
| 2003/0039938 | A1 * | 2/2003 | Orikasa | A61C 7/287 433/11 |
| 2004/0170942 | A1 * | 9/2004 | Heiser | A61C 7/28 433/11 |
| 2006/0204918 | A1 * | 9/2006 | Voudouris | A61C 7/287 433/11 |
| 2006/0228662 | A1 * | 10/2006 | Lokar | A61C 7/287 433/8 |
| 2006/0228664 | A1 * | 10/2006 | Castner | A61C 7/287 433/11 |
| 2006/0263737 | A1 * | 11/2006 | Oda | A61C 7/12 433/10 |
| 2007/0009849 | A1 * | 1/2007 | Wool | A61C 7/287 433/10 |
| 2007/0166658 | A1 * | 7/2007 | Voudouris | A61C 7/285 433/10 |
| 2007/0243497 | A1 * | 10/2007 | Voudouris | A61C 7/141 433/10 |
| 2007/0269763 | A1 * | 11/2007 | Schendell-Groling | A61C 7/287 433/10 |
| 2007/0275342 | A1 * | 11/2007 | Oda | A61C 7/287 433/10 |
| 2008/0311534 | A1 * | 12/2008 | Farzin-Nia | A61C 7/20 433/11 |
| 2009/0075227 | A1 * | 3/2009 | Opin | A61C 7/02 433/11 |
| 2009/0325120 | A1 * | 12/2009 | Lewis | A61C 7/287 433/13 |
| 2010/0062387 | A1 * | 3/2010 | Hilliard | A61C 7/22 433/11 |
| 2010/0311004 | A1 * | 12/2010 | Voudouris | A61C 7/14 433/11 |
| 2011/0076633 | A1 * | 3/2011 | Bryant | A61C 7/287 433/11 |
| 2011/0318699 | A1 * | 12/2011 | Forster | A61C 7/287 433/10 |

FOREIGN PATENT DOCUMENTS

| | | |
|---|---|---|
| JP | 10-192302 A | 7/1998 |
| JP | 2001-503305 A | 3/2001 |
| JP | 2004-255190 A | 9/2004 |
| JP | 2004-526484 A | 9/2004 |
| JP | 4411573 B2 | 2/2010 |
| JP | 4444410 B2 | 3/2010 |

OTHER PUBLICATIONS

International Search Report (PCT/ISA/210), dated Oct. 18, 2011, issued by the International Searching Authority in counterpart International Patent Application No. PCT/JP2011/070639.
Invoice dated Aug. 14, 2009 on the purchase of a starter kit and extract from Ifax archive of delivery of starter kit order. TMP3 and TMP3a (2 pages total).
Notice of Opposition dated Sep. 19, 2016 issued by the European Patent Office in counterpart European Patent Application No. 11825099.2.
Notification of Reasons for Refusal dated Nov. 4, 2015 by the Japanese Patent Office in related Application No. 2012-265129.
Office Action dated May 7, 2015 issued by Japanese Patent Office in counterpart Japanese Patent Application No. 2012-265129.
Photograph of front side and rear side of a QuicKlear brackets starter kit from the year 2009. Annex TMP4 (2 pages total).
Photographs of scaled enlarged demonstration model of a QuicKlear bracket. Annex TMP5 (5 pages total).
Report on the presentation of the QuicKlear brackets on hte IDS fair on p. 21 in No. 5 of the magazine Kieferorthopadische Nachrichten dated May 2009. TMP2 (2 pages total).
Written Opinion (PCT/ISA/237), dated Oct. 18, 2011, issued by the International Searching Authority in counterpart International Patent Application No. PCT/JP2011/070639.
European Search Report dated Jul. 4, 2014 from the European Patent Office corresponding international Application No. 11825099.2.

* cited by examiner

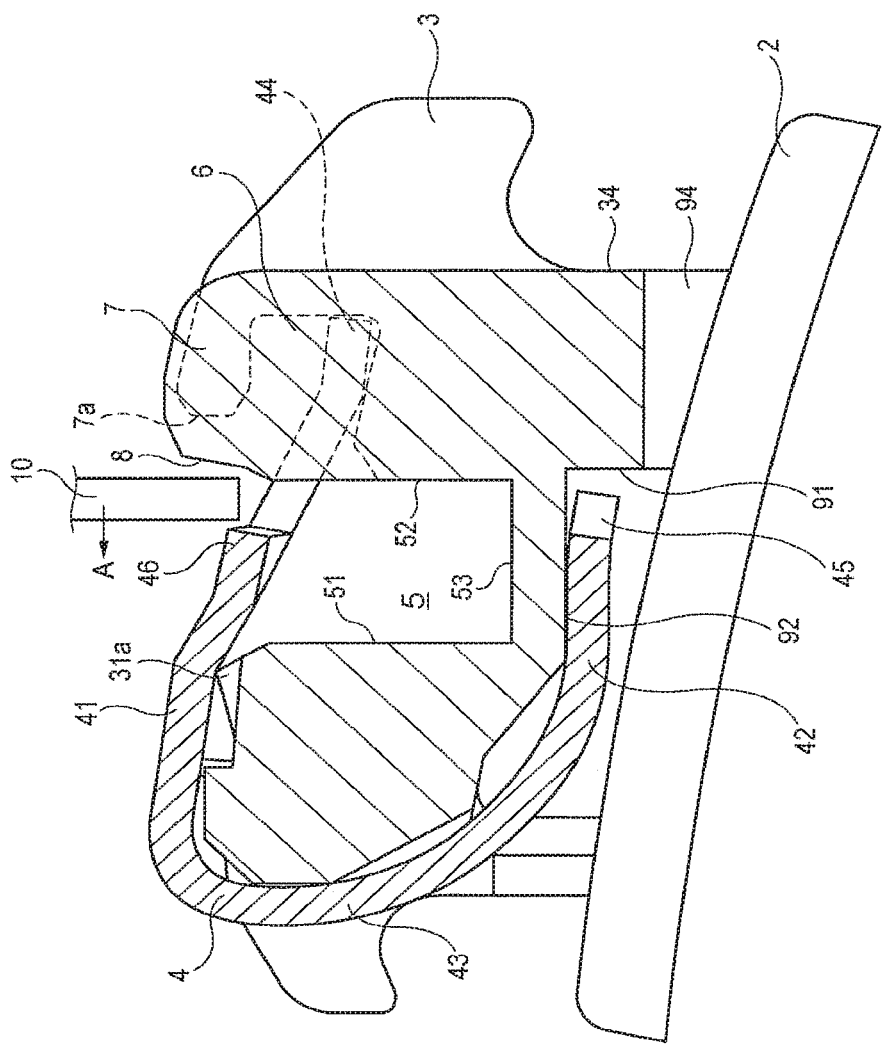

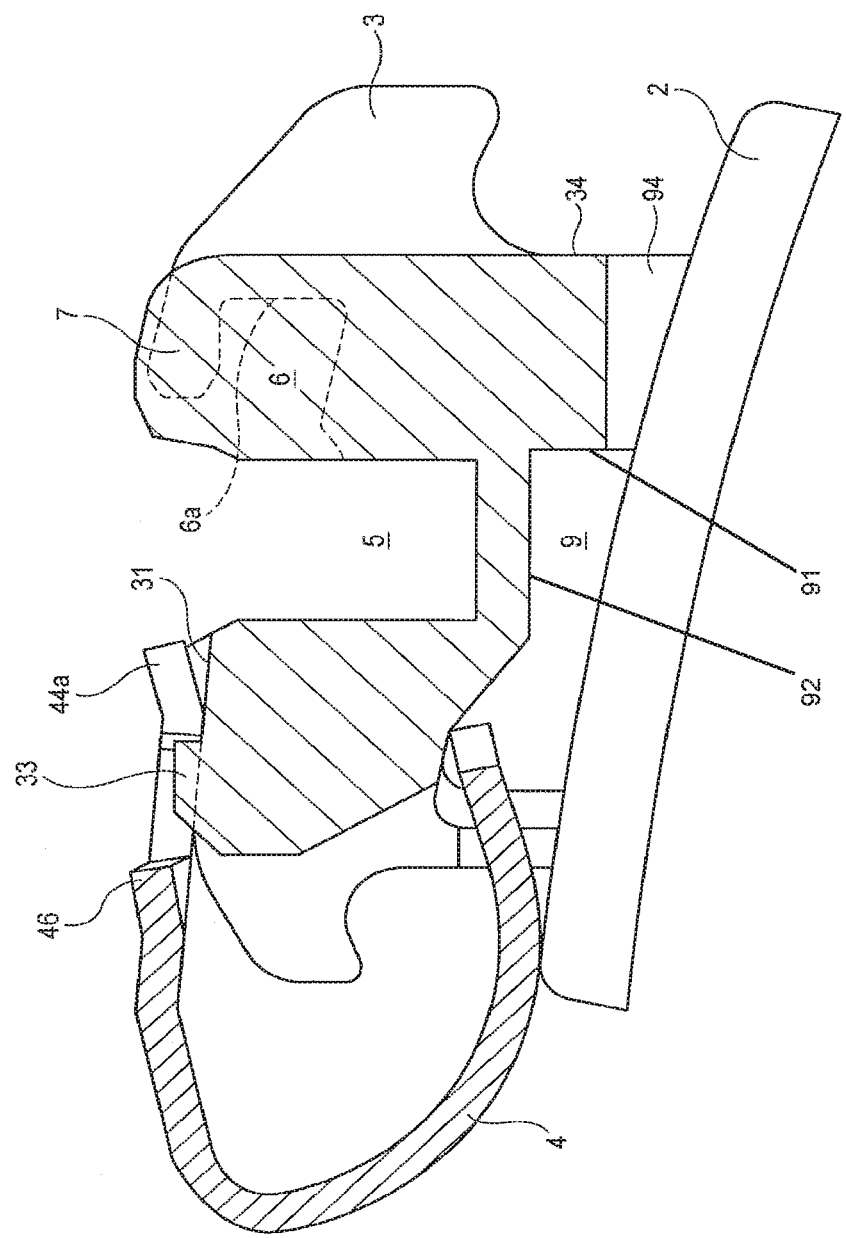

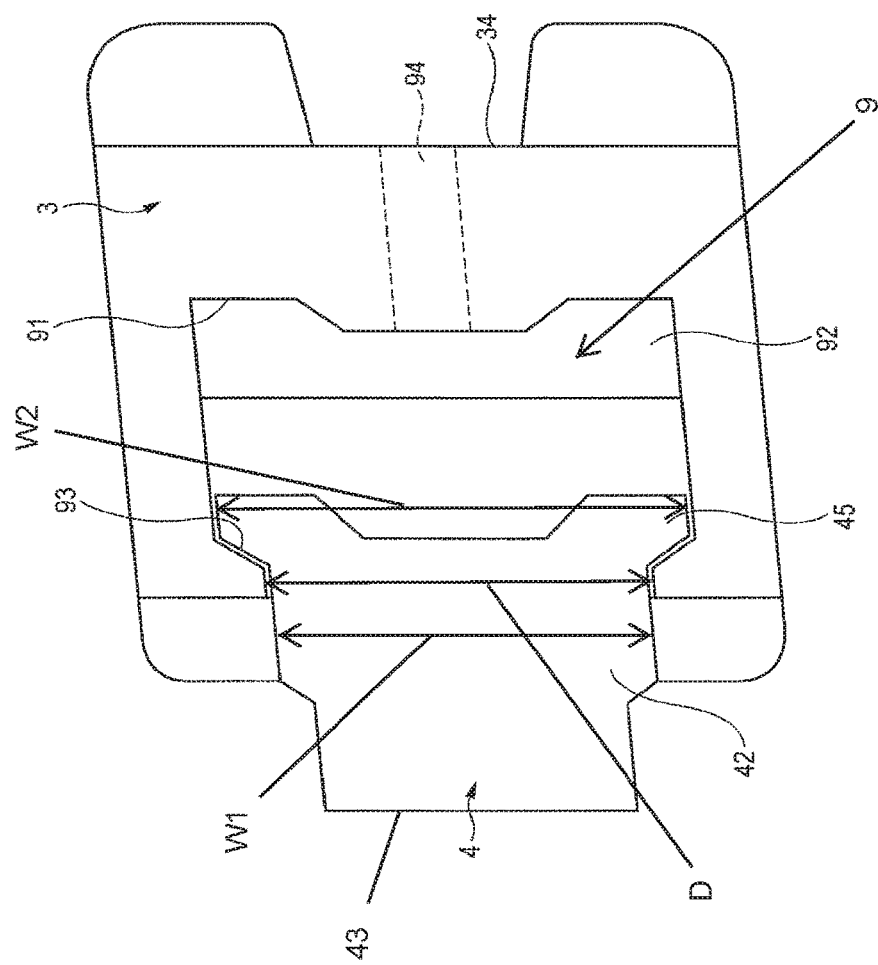

ORTHODONTIC BRACKET

CROSS-REFERENCE TO RELATED APPLICATION

This application is a Continuation-In-Part of application Ser. No. 13/819,797 filed on Feb. 28, 2013, which is a National Stage application of International Patent Application No. PCT/JP2011/070639, filed on Sep. 9, 2011, which claims priority to Japanese Patent Application No. 2010-210121, filed Sep. 17, 2010, in the Japanese Patent Office, the entire disclosures of each of which are herein incorporated by reference in their entirety.

BACKGROUND

1. Field

Apparatuses, devices, and articles of manufacture consistent with the present disclosure relate to an orthodontic bracket which is used for correcting a misaligned tooth or a twisted tooth.

2. Description of Related Art

Conventionally, on occasion of conducting an orthodontic treatment, there has been employed a ligating method in which ligation is performed by inserting an archwire into an archwire slot of an orthodontic bracket which is attached to a tooth of a patient, and by hooking a ligating tool such as a ligature ring formed of resin or a ligature wire formed of stainless steel on tie wings of the orthodontic bracket so as to prevent the archwire from being undesirably detached from the orthodontic bracket.

On the other hand, an orthodontic bracket requiring no ligating work which is called "a self-ligating bracket" has been disclosed. In case where the self-ligating bracket is used for treatment, the ligating tool such as the ligature ring or ligature wire is eliminated, and therefore, it is possible for a doctor to reduce the time (i.e., a "chair time") for applying the treatment to a patient. In addition, food residue that sticks to the orthodontic bracket and the ligating tool, after the ligating tool has been attached, will not occur, and therefore, it is possible to keep the mouth hygienic and reduce the occurrence of cavities.

The self-ligating bracket as described above may be provided with a clip of a sliding type or a rotary type. By moving the clip, the archwire may be inserted in the archwire slot or may be detached from the archwire slot, and after insertion, the clip holds the archwire in the slot.

SUMMARY

It is an aspect is to provide an orthodontic bracket which has a low height from a tooth on which the orthodontic bracket is mounted while reducing a possibility that a clip of the orthodontic bracket may be undesirably opened such that an archwire is undesirably detached from the orthodontic bracket.

According to an aspect of an example embodiment, there is provided an orthodontic bracket comprising a base part; a bracket body mounted on the base part; a clip having a U-shaped cross-section, the clip being mounted on the bracket body and comprising an upper part along an upper face of the bracket body, a lower part along a lower face of the bracket body, and a curved part therebetween; an archwire slot in the upper face of the bracket body that extends perpendicular to a moving direction of the clip; an engaging part for receiving a first end of the clip provided on a side face of the archwire slot opposite to the curved part; a guide groove for guiding the lower part of the clip in the moving direction of the clip is provided on the lower face under the archwire slot; a tool guiding face provided at a center of the engaging part in a longitudinal direction of the engaging part; and a space for receiving a tool for opening the clip provided adjacent to the tool guiding face, wherein, in a state of insertion, the lower part is below a bottom face of the archwire slot and a second end of the clip does not pass through an end face of the bracket body at an opposite side from the curved part, wherein a lower extended part of the clip does not extend past the archwire slot in a locked position in which the first end is received into the engaging part, and wherein the guide groove is provided underneath the archwire slot such that the guide groove is positioned on a hypothetical line drawn perpendicular to a bottom portion of the archwire slot and passing through the bottom portion of the archwire slot.

According to another aspect of an example embodiment, there is provided an orthodontic bracket comprising a base part; a bracket body mounted on the base part; a clip having a U-shaped cross-section, the clip being mounted on the bracket body and comprising an upper part along an upper face of the bracket body, a lower part along a lower face of the bracket body, and a curved part therebetween; an archwire slot in the upper face of the bracket body that extends perpendicular to a moving direction of the clip; an engaging part for receiving a first end of the clip provided on a side face of the archwire slot opposite to the curved part; a guide groove for guiding the lower part of the clip in the moving direction of the clip is provided on the lower face under the archwire slot; a tool guiding face provided at a center of the engaging part in a longitudinal direction of the engaging part; and a space for receiving a tool for opening the clip provided adjacent to the tool guiding face, wherein, in a state of insertion, the lower part is below a bottom face of the archwire slot and a second end of the clip does not pass through an end face of the bracket body at an opposite side from the curved part, wherein a lower extended part of the clip does not extend past the archwire slot in a locked position in which the first end is received into the engaging part, wherein the guide groove is provided underneath the archwire slot such that the guide groove is positioned on a hypothetical line drawn perpendicular to a bottom portion of the archwire slot and passing through the bottom portion of the archwire slot, wherein the second end of the clip is provided with an enlarged width part, and the guide groove is provided, at a side of the curved part, with clip retaining parts that protrude inward from sides of the guide groove such that a distance between the clip retaining parts is smaller than a width of the enlarged width part of the clip.

According to another aspect of an example embodiment, there is provided an orthodontic bracket comprising a base part; a bracket body mounted on the base part, the bracket body comprising a retaining projection provided on an upper face thereof; a clip having a U-shaped cross-section, the clip being mounted on the bracket body and comprising an upper part along the upper face of the bracket body, a lower part along a lower face of the bracket body, a curved part therebetween, and an engaging hole provided in the upper part of the clip in a position that corresponds to a position of the retaining projection of the bracket body such that the retaining projection projects through the engaging hole when the clip is in an open position thereon; and an archwire slot in the upper face of the bracket body that extends perpendicular to a moving direction of the clip.

BRIEF DESCRIPTION OF THE DRAWINGS

The above and/or other aspects will become apparent and more readily appreciated from the following description of example embodiments, taken in conjunction with the accompanying drawings of which:

FIG. 2 is a sectional view of the orthodontic bracket as shown in FIG. 1 in a closed state of a slot;

FIG. 3 is a sectional view of the orthodontic bracket as show in FIG. 1 in an opened state of the slot;

FIG. 4 is a bottom view of a bracket body of the orthodontic bracket as shown in FIG. 1;

DETAILED DESCRIPTION

Below exemplary embodiments will be described with reference to the drawings. It is noted that the drawings are not to scale and dimensions may be exaggerated in some cases for clarity and simplicity of description. However, the present disclosure is not limited to the specific exemplary embodiments described herein, but rather encompasses all modifications, equivalents, and substitutions without departing from the scope and spirit of the present disclosure.

Figure 10:
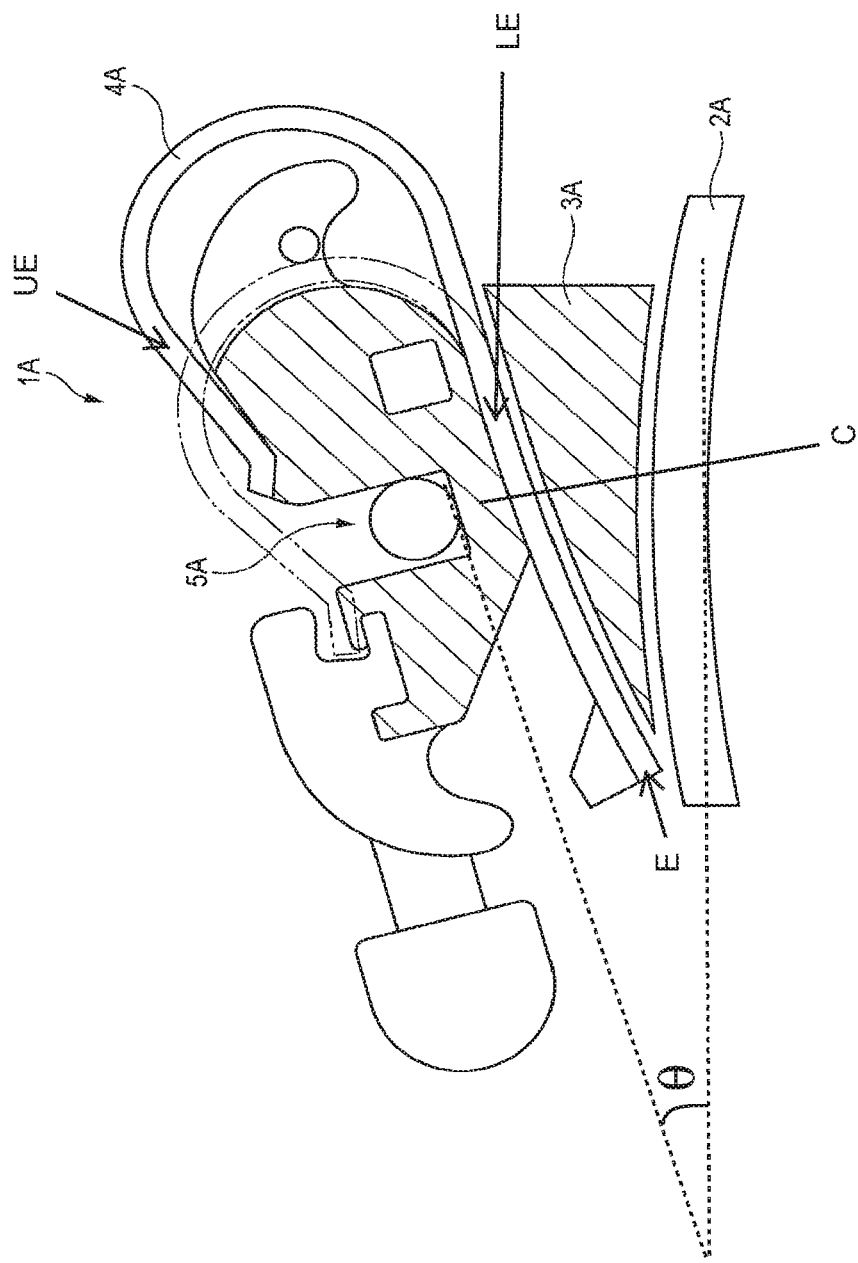
FIG. 10 is a view showing a related art orthodontic bracket having a clip of a sliding type.

FIG. 10 shows an orthodontic bracket 1A provided with a clip 4A of a sliding type, FIG according to the related art. A lower extended part LE of the clip 4A is formed longer than an upper extended part UE. For this reason, in case where the clip 4A is inserted at a large angle with respect to a base part 2A of the orthodontic bracket, depending on a curvature of a surface of a tooth to be treated or an angle of the base part (torque), there is a disadvantage that an extended end E of the lower extended part LE may interfere with the base part 2A or the tooth, when the clip 4A is inserted up to a slot closing position. For the purpose of preventing this interference, a wall thickness of a bracket body 3A in a part C below a slot 5A is formed thickly.

The reason for the above will be described in detail herein below.

When an orthodontic treatment employing the orthodontic bracket of a torque-in base type such as the one shown in FIG. 10 is conducted, it is necessary to directly or indirectly attach a plurality of the orthodontic brackets 1A to the teeth. On this occasion, a curvature of a tooth face and a position where the orthodontic bracket 1A is to be attached are sometimes different between teeth of an upper jaw and a lower jaw, and between an anterior tooth and a posterior tooth. As a result, in the orthodontic bracket 1A which has been attached to a specific tooth, an angle θ provided between a bottom face of the slot 5A and the base part 2A which is fixed along a contour of the tooth face may become large, in some cases.

Under these circumstances, in order to prevent interference between the base part 2A and the clip 4A, it is considered, for example, to design the orthodontic bracket 1A in such a manner that a sliding direction of the clip 4A is parallel to the bottom face of the slot 5A as shown in FIG. 10. However, in this case, it is necessary to make the thickness of the part C below the slot 5A larger so that the lower extended part LE of the clip 4A can pass through without interference. This is because in case where the thickness of the part C below the slot 5A is small, the extended end E of the lower extended part LE of the clip 4A may interfere with the base part 2A, and the clip 4A cannot be slid up to a desired position, such as a position to close the archwire slot 5A.

Particularly in the clip 4A of the sliding type shown in FIG. 10, the extended end E of the lower extended part LE is so formed as to pass through the bracket body 3A. Accordingly, the lower extended part LE is formed longer, and the part C of the bracket body 3A below the slot 5A tends to have a larger thickness for the purpose of avoiding interference. In case where the part C below the slot 5A is formed thick as described above, and a total height of the bracket is increased, there is a disadvantage that a back side of a lip of the patient is likely to touch the orthodontic bracket 1A, and the patient may feel uncomfortable.

Figure 11:
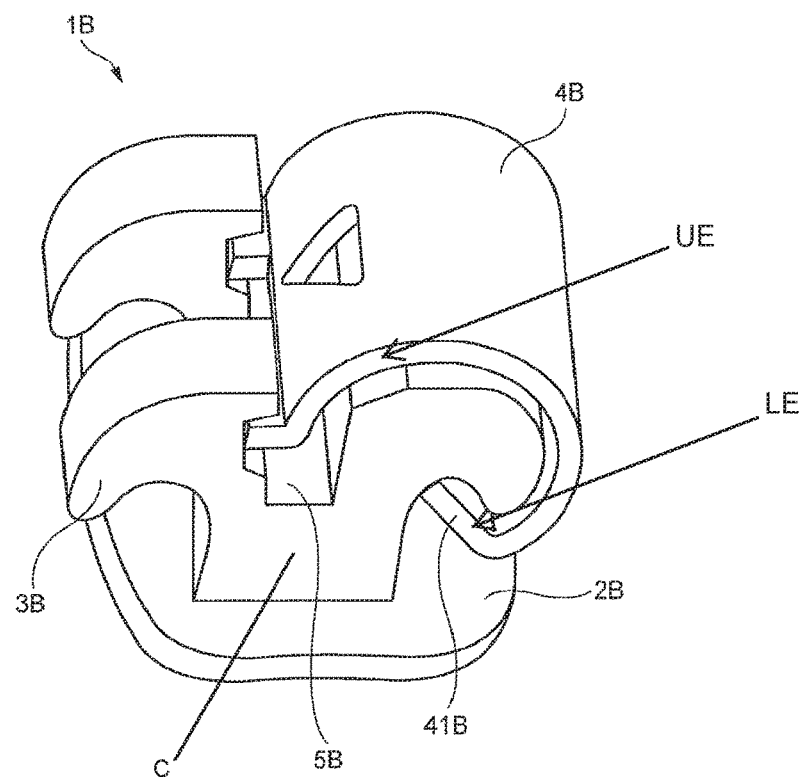
FIG. 11 is a view showing a related art orthodontic bracket having a clip of a rotary type.
Figure 12:
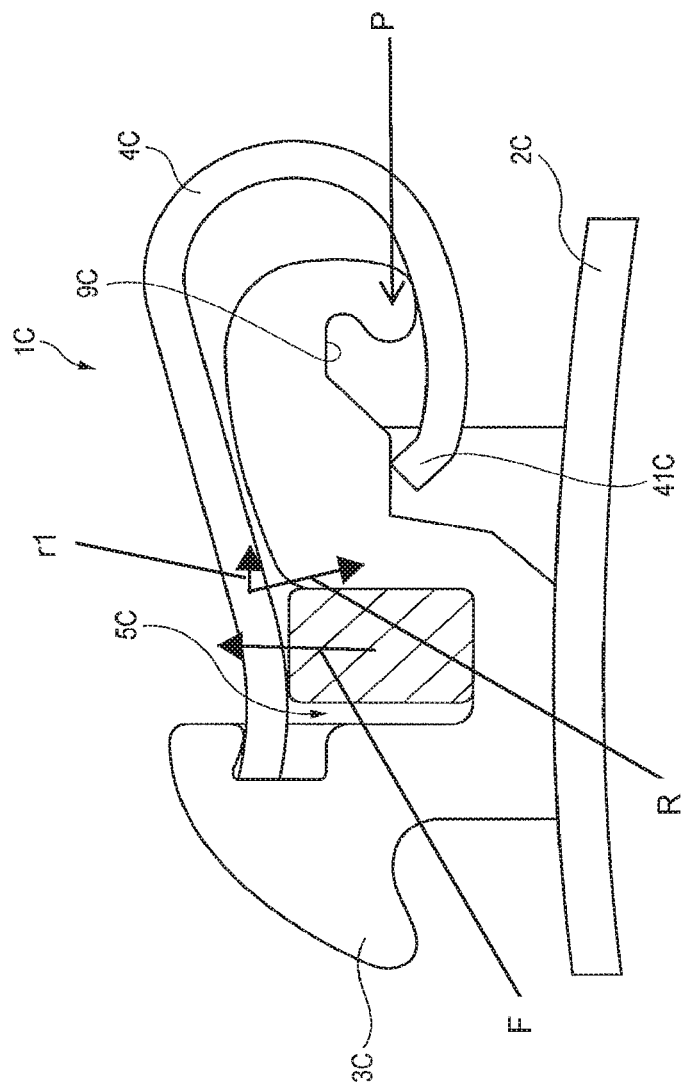
FIG. 12 is a view showing another related art orthodontic bracket having a clip of a rotary type.

On the other hand, FIGS. 11 and 12 show orthodontic brackets that adopt clips of a rotary type. As shown in FIG. 11, in an orthodontic bracket 1B, the clip 4B is rotated around its lower end 41B, and thus, a slot 5B may be opened. A lower extended part LE of the clip 4B of the rotary type is shorter than that of the aforesaid clip 4A of the sliding type. Accordingly, the bracket body 3B does not need to have a large wall thickness in the part C below the slot 5B, and thus the orthodontic bracket 1B may be made smaller in height.

However, the orthodontic bracket 1B provided with the clip 4B of the rotary type has a disadvantage in that the archwire is likely to be undesirably detached. For example, an unexpected strong force may be applied to the archwire, in some cases, for example when the patient bites a hard food, or when the archwire is caught by something during the orthodontic treatment. On this occasion, a force in a direction of withdrawing the archwire from the slot 5B is exerted on the archwire, and the archwire tends to lift the upper extended part UE of the clip 4B. As a result, there have been such cases that the clip 4B is undesirably rotated to open the slot 5B, and the archwire is undesirably detached, and that the clip 4B is deformed, and the orthodontic bracket 1B must be exchanged.

FIG. 12 also shows an orthodontic bracket 1C that adopts a clip 4C of the rotary type. The orthodontic bracket 1C is opened and closed in two steps. In the orthodontic bracket 1C, the clip 4C is first slid sideward to displace a lower end 41C of the clip 4C to a rotating part 9C, and thereafter, the lower end 41C of the clip 4C is rotated around part P of the bracket base 3C. In this manner, the slot 5C may be opened. The steps are repeated in opposite order to close the slot 5C.

However, the orthodontic bracket 1C also has a similar disadvantage to the orthodontic bracket 1B shown in FIG. 11. In the clip 4C having the structure shown in FIG. 12, when a force F in a direction of withdrawing the archwire from the slot 5C is exerted on the archwire, such that a force for lifting the upper extended part UE of the clip 4C is applied, the clip 4C moves sideward by a component r1 of an elastic restoring force R of the clip 4C. As a result, there have been such cases that the clip 4C is rotated undesirably to undesirably open the slot 5C, and the archwire is undesirably detached, and that the clip 4C is deformed, and the orthodontic bracket 1C must be exchanged.

Under the circumstances, exemplary embodiments herein have been made in view of the above described disadvantages with the related art, and an aspect is to provide an orthodontic bracket which has a low height while reducing a possibility that the clip may be undesirably opened such that the archwire is undesirably detached from the slot.

Hereinafter, various exemplary embodiments will be described in greater detail with reference to the accompanying drawings.

<First Exemplary Embodiment>

Figure 1:
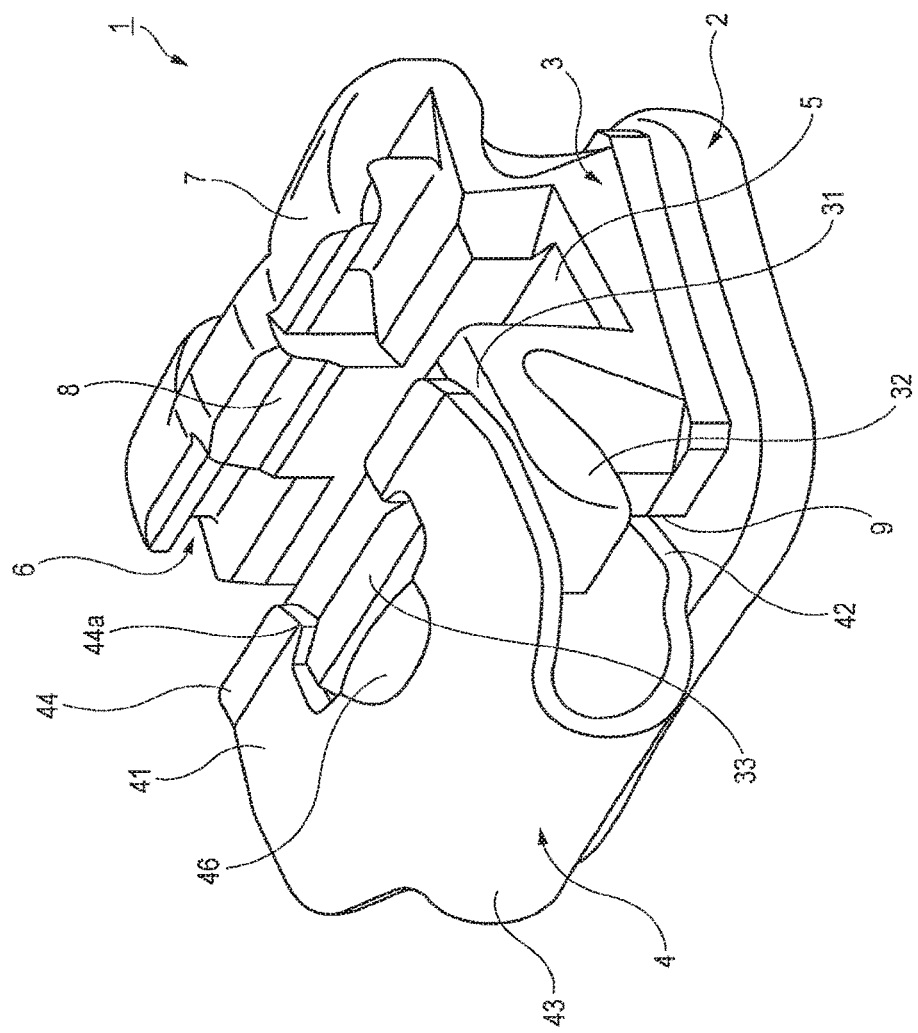
FIG. 1 is a perspective view of an orthodontic bracket according to a first exemplary embodiment.

An orthodontic bracket 1 according to a first exemplary embodiment will be described referring to FIGS. 1 to 4. FIG. 1 is a perspective view of the orthodontic bracket 1, in a state where a slot is opened. FIG. 2 is a sectional view of the orthodontic bracket 1 as shown in FIG. 1, taken along a plane containing an engaging part 6. FIG. 3 is a sectional view of the orthodontic bracket 1, taken along the same plane as in FIG. 2, in a state where the slot is opened. FIG. 4 is a bottom view of a bracket body 3.

As shown in FIG. 1, the orthodontic bracket 1 has a base part 2 in a plate-like shape which can be directly or indirectly fixed to a surface of a tooth at its bottom face, a bracket body 3 which is fixed to an upper face of the base part 2, and a clip 4 which is mounted on the bracket body 3 so as to move relative to the bracket body 3. The bracket body 3 in the first exemplary embodiment shown in FIGS. 1-4 is a bracket of a twin type provided with two pairs of wings which are arranged in parallel. It is to be noted that in the following description, a bottom face side of the base part 2 to be fixed to the tooth face is denoted as "a lower side", and a surface side of the base part 2 on which the bracket body 3 is mounted is denoted as "an upper side".

(Bracket Body 3)

As shown in FIGS. 1 and 2, an upper supporting face 31 for supporting an upper extended part 41 of the clip 4 in sliding contact therewith is provided on an upper face of the bracket body 3 (at an opposite side to the base part 2), and a guide groove 9 for guiding a lower extended part 42 of the clip 4 is provided on a lower face of the bracket body 3 (a face close to the base part 2). In this manner, the clip 4 is held on the bracket body 3 so as to move relative to the bracket body 3.

Moreover, the bracket body 3 has a pair of right and left protruded parts 32 which are formed at a side of the bracket body 3 on which the clip 4 is mounted. The protruded parts 32 restrict a position of a curved part 43 of the clip 4, when an archwire slot 5 is closed by the clip 4 (at a slot closing time). Further, a retaining projection (an excessive opening preventing projection) 33 is provided on the upper supporting face 31. In other words, the retaining projection 33 prevents the clip 4 from falling off of the bracket body 3 when the clip 4 is slid to open the archwire slot 5.

As shown in FIG. 2, the bracket body 3 is provided with an overriding step part 31a on the upper supporting face 31 at a side close to the archwire slot 5. The overriding step part 31a comes into contact with an upper end 44 of the clip 4, when the archwire slot 5 is not closed by the clip 4 (i.e., at a slot opening time). In this manner, the clip 4 is prevented from being unintentionally moved toward the archwire slot 5 to unintentionally close the archwire slot 5. In other words, the overriding step part 31a prevents the clip 4 from sliding unintentionally under its own weight back into a closed position from an opened position.

(Clip 4)

The clip 4 is an elastically deformable member having a substantially U-shape in section. The clip 4 includes the upper extended part 41 having a planar shape and extending along the upper face of the bracket body 3, the lower extended part 42 having a planar shape and extending along the lower face of the bracket body 3, and the curved part 43 which interconnects the upper extended part 41 and the lower extended part 42. A lower end 45 of the lower extended part 42 is extended up to a position below a bottom face 53 of the archwire slot 5. That is, the lower end 45 is in a position below the bottom face 53 of the archwire slot 5 when the clip 4 is in a closed position.

The clip 4 is curved in such a manner that there is the smallest distance between the upper end 44 and the lower end 45. In other words, the distance between the upper end 44 and the lower end 45 is smaller than a distance between other portions of the upper extended part 41 and the lower extended part 42. In the first exemplary embodiment shown in FIGS. 1-4, the curved part 43 of the clip 4 is so formed as to have a smaller radius of curvature at an upper side to be continued to the upper extended part 41, and a larger radius of curvature at a lower side to be continued to the lower extended part 42. In other words, the curved part 43 of the clip 4 has an upper radius of curvature and a lower radius of curvature, and the upper radius of curvature at the upper side is smaller than the lower radius of curvature at the lower side. Because the upper radius of curvature at the upper side is smaller than the lower radius of curvature at the lower side, the clip 4 will not be prolonged in an upward direction. In other words, a distance between the upper extended part 41 and the lower extended part 42 may be kept as short as possible. As a result, a height of the clip 4 may be reduced compared to the related art.

Moreover, as shown in FIG. 1, the clip 4 in the first exemplary embodiment is formed in a bifurcated shape in such a manner that both left and right ends of the upper end 44 in a lateral direction (a longitudinal direction of the archwire slot 5) protrude. Moreover, the upper end 44 of the clip 4 is provided with a tool locking projection 46 which is projected upward, at an intermediate portion between the left and right ends of the upper end 44 in the lateral direction.

The tip ends of the bifurcated shape of the upper end 44 of the clip 4 are formed as a pair of right and left inward projections (excessive opening preventing parts) 44a which can be engaged with the retaining projection 33 of the bracket body 3. The right and left inward projections 44a are so formed as to be smaller in width at their ends. While the archwire slot 5 is opened, the inward projections 44a are engaged with the retaining projection 33 of the bracket body 3 thereby to prevent the clip 4 from being opened too much. As a result, an excessive force will not be exerted on the clip 4.

(Archwire Slot 5)

The archwire slot 5 for containing an archwire is formed on the upper face of the bracket body 3 along a direction substantially perpendicular to a moving direction of the clip 4 with respect to the bracket body 3. As shown in FIGS. 2 and 3, the archwire slot 5 is formed as a groove having a substantially U-shape in section which is open upward. The archwire slot 5 includes a first side face 51 at a curved part side which is close to the curved part 43 of the clip 4, a second side face 52 at an opposite side to the curved part which is opposed to the first side face 51 at the curved part side, and the bottom face 53 which interconnects the first side face 51 and the second side face 52.

A pair of right and left engaging parts 6 are formed on the second side face 52 at the opposite side to the curved part of the archwire slot 5. The engaging parts 6 are recessed to an opposite side of the bracket body 3 from the clip 4, so that the bifurcated ends of the upper end 44 of the clip 4 may be inserted respectively therein.

Moreover, hood parts (wire retaining hood parts) 7 are provided above the engaging parts 6 respectively so as to overhang from upper ends of the engaging parts 6 toward the curved part of the clip 4. Even though the archwire tends to lift the upper extended part 41 of the clip 4, while the slot is closed as shown in FIG. 2, the hood parts 7 come into contact with the upper extended part 41 thereby to prevent the clip 4 from being withdrawn from the engaging parts 6.

Overhanging ends 7a of the hood parts 7 are positioned more remote from the curved part of the clip 4 than the second side face 52 at the opposite side to the curved part of the archwire slot 5. This is because in case where the overhanging ends 7a are extended up to a position near the second side face 52, a wall thickness of the hood parts 7 is inevitably made larger for the purpose of securing rigidity of the hood parts 7 which is required for preventing withdrawal of the clip 4, and accordingly, a total height of the orthodontic bracket 1 is increased. By contrast, since the overhanging ends 7a are not extended up to a position of the second side face 52, the wall thickness of the hood parts 7 may be less thick than the case where the overhanging ends 7a are extended up to the position of the second side face 52, and thus the hood parts 7 may provide strong securing rigidity while decreasing the total height of the orthodontic bracket 1.

Moreover, a tool guiding face 8 is formed between the pair of the engaging parts 6, as shown in FIG. 1. The tool guiding face 8 is a face which is formed flush with the second side face 52 at the opposite side to the curved part of the archwire slot 5. To open the archwire slot 5, an opening tool 10 is inserted between the tool guiding face 8 and the tool locking projection 46 of the clip 4, as described below. An upper part of the tool guiding face 8 is formed as a taper face which is open upward. In this manner, a tip end of the opening tool 10 can be easily inserted between the tool locking projection 46 and the tool guiding face 8.

(Guide Groove 9)

As shown in FIGS. 3 and 4, a guide groove 9 is formed in a lower part of the bracket body 3. As shown in FIG. 4, the guide groove 9 is formed in a substantially U-shape which is open toward the curved part 43, as seen from a bottom face side. The guide groove 9 is extended along the moving direction of the clip 4 with respect to the bracket body 3, from a position near the curved part 43 of the clip 4 up to a butting wall 91 which is provided at a position generally below the archwire slot 5.

A width of the guide groove 9 is set to be slightly larger than a width of the lower end 45 of the lower extended part 42 of the clip 4. The lower extended part 42 of the clip 4 is inserted into a space which is formed between the guide groove 9 and the upper face of the base part 2. The lower extended part 42 is guided by the guide groove 9, and hence, the clip 4 may be moved with respect to the bracket body 3.

When the lower extended part 45 of the clip 4 is butted against the butting wall 91 of the guide groove 9, further insertion of the clip 4 is restricted. The butting wall 91 is provided at a position below the side face 52 at the opposite side to the curved part of the archwire slot 5. Accordingly, the lower end 45 of the clip 4 is positioned below the archwire slot 5, while the slot is closed.

Moreover, a flat face part 92 is formed so as to extend from the butting wall 91 of the guide groove 9 toward the curved part 43 of the clip 4. The flat face part 92 is formed substantially in parallel with the bottom face 53 of the archwire slot 5.

In addition, the guide groove 9 is provided, in its end part at the curved part side, with a pair of retaining parts (clip retaining parts) 93 which protrude inward so as to make a distance between the retaining parts smaller. The lower end 45 of the clip 4 has a larger width than a width of the lower extended part 42. Because the clip retaining parts 93 hold the lower end 45 of the clip 4, the lower extended part 42 of the clip 4 is prevented from dropping from the guide groove 9. For this purpose, the distance D between the pair of the clip retaining parts 93 of the bracket body 3 is so formed as to be larger than the width W1 of the lower extended part 42 of the clip 4, and as to be smaller than the width W2 of the lower end 45 of the clip 4.

Further, a through groove (a through part) 94 for removing a foreign body is provided at the opposite side of the guide groove 9 from the curved part 43 of the clip 4 so as to pass through the bracket body 3 up to an end face 34 at the opposite side of the bracket body 3 from the curved part 43 of the clip 4. Accordingly, even during the orthodontic treatment where the orthodontic bracket 1 is mounted on a tooth, it is possible to remove a foreign body (such as food particles) sticking inside the guide groove 9, by cleaning the guide groove 9 with a water pick or the like from an exterior of the orthodontic bracket 1, by way of the through groove 94. In this manner, the mouth of the patient may be kept hygienic to avoid cavities. Moreover, it is possible to prevent such a disadvantage that the clip 4 cannot be opened due to the foreign body which has entered between the clip 4 and the guide groove 9.

A width of the through groove 94 is set to be smaller than the width of the lower end 45 of the clip 4, so that the lower end 45 of the clip 4 cannot enter into the through groove 94. As a result, the lower end 45 of the clip 4 will not reach the end face 34 at the opposite side of the bracket body 3 from the curved part 43 of the clip 4.

When the orthodontic treatment is conducted, the orthodontic brackets 1 each having the above described structure are respectively attached to a plurality of teeth, and the archwires are inserted into the archwire slots of the respective orthodontic brackets 1. Further, in a state where the archwire slots 5 are closed with the clips 4 to prevent the withdrawal of the archwires, an orthodontic force in a direction of correcting dentition is applied to the teeth by way of the orthodontic brackets 1.

(Slot Closing Operation and Slot Opening Operation)

In order to proceed from a closed state of the slot in FIG. 2 to an open state of the slot in FIG. 3, as a first step, the tip end of the opening tool 10 is inserted between the tool locking projection 46 and the tool guiding face 8, as shown in FIG. 2. After the tip end of the opening tool 10 is hooked on the tool locking projection 46, the opening tool 10 is moved together with the clip 4 in a direction of an arrow mark A in FIG. 2, in such a manner that the upper ends 44 of the clip 4 are withdrawn from the hood parts 7.

When the upper ends 44 of the clip 4 are withdrawn from the hood parts 7, the clip 4 is first withdrawn in the lateral direction (to a left side in FIG. 2), while a moving direction of the lower end 45 is restricted within the flat face part 92 of the guide groove 9. Then, the lower end 45 comes into contact with the retaining parts 93, and a lateral movement of the clip 4 is stopped. In a state where the lower end 45 is in contact with the retaining parts 93, the clip 4 is rotated around the lower end 45 which is in contact with the clip retaining parts 93, as a rotation center. In this manner, the archwire slot 5 is opened.

Because withdrawal of the lower end 45 of the clip 4 is thus prevented by the retaining parts 93, the clip 4 is prevented from dropping from the bracket body 3. Even in case where the archwire slot 5 is opened after the orthodontic bracket 1 has been attached to the tooth, for example, for the purpose of exchanging the archwire, the clip 4 will not drop from the bracket body 3. Therefore, the orthodontic bracket 1 can be easily treated.

When the slot is closed, the clip 4 is first rotated around the lower end 45 which is in contact with the clip retaining parts 93, as the rotation center. Thereafter, the clip 4 is slid in the lateral direction along the flat face part 92, thereby allowing the upper ends 44 to be inserted into the engaging parts 6. On this occasion, the upper ends 44 are rotated downward along with the rotation of the clip 4, and in a state where the upper ends 44 are lowered, the clip 4 is laterally moved toward the hood parts 7. Because the hood parts 7 into which the upper ends 44 are inserted can be formed at a lower position as discussed above, it is possible to reduce the total height of the orthodontic bracket 1.

(Operation)

According to the orthodontic bracket 1 in the above described first exemplary embodiment, even in the closed state of the archwire slot 5 as shown in FIG. 2, the lower extended part 42 of the clip 4 will not pass through the bracket body 3 up to the end face 34 at the opposite side of the bracket body 3 from the curved part 43, and the lower end 45 of the clip 4 is positioned below the archwire slot 5. Accordingly, the lower extended part 42 of the clip 4 may be made shorter, as compared with the related art orthodontic bracket provided with the clip of the sliding type as shown for example in FIG. 10.

Particularly, as compared with the related art orthodontic bracket provided with the clip of the sliding type in which the part C below the archwire slot is formed thicker as shown in FIG. 10, in the orthodontic bracket 1 according to the first exemplary embodiment shown in FIGS. 1-4, the thickness of the part below the archwire slot 5 can be made smaller, because the lower extended part 42 is shorter, and will not interfere with the tooth face. As the results, it is possible to reduce the total height of the orthodontic bracket 1. In this manner, the patient equipped with the orthodontic bracket 1 scarcely feels uncomfortable.

During the orthodontic treatment, when a force for withdrawing the archwire from the archwire slot 5 is exerted on the archwire, the archwire applies an upwardly pushing force to the upper extended part 41 of the clip 4. On this occasion, the lower extended part 42 of the clip 4 receives a repulsive force from the guide groove 9. Because the lower extended part 42 of the clip 4 is extended up to the position below the bottom face 53 of the archwire slot 5, the upper extended part 41 and the lower extended part 42 of the clip 4 are subjected to the forces from above and below via the archwire slot 5. Accordingly, the forces to be exerted on the clip 4 are cancelled by each other, and hence, a rotation moment will not be exerted on the clip 4. Therefore, according to the orthodontic bracket 1 in the first exemplary embodiment shown in FIGS. 1-4, the clip 4 will not be unintentionally rotated, and there is an advantage in that the archwire slot 5 will not unintentionally be opened.

In the related art clip of the rotary type as shown in FIGS. 11-12, the lower end of the clip is extended only up to a lower part at the curved part side than the archwire slot. That is, the lower end of the clip does not extend to a position below the archwire slot 5B or 5C. For this reason, when a force for withdrawing the archwire from the archwire slot 5B or 5C is exerted on the archwire, the forces exerted on the upper extended part and the lower extended part are not cancelled by each other, and there is the disadvantage that the archwire may drop from the bracket body.

By contrast, in the first exemplary embodiment shown in FIGS. 1-4, the archwire is guided by the first side face 51 and the second side face 52 of the archwire slot 5, and therefore, the force from the archwire is exerted on the upper extended part 41 of the clip 4 perpendicularly to the bottom face 53 of the archwire slot 5. Moreover, the flat face part 92 of the guide groove 9 is formed substantially in parallel with the bottom face 53 of the archwire slot 5, and therefore, the repulsive force from the flat face part 92 of the guide groove 9 is exerted on the lower extended part 42 of the clip 4 perpendicularly to the bottom face 53 of the archwire slot 5. Therefore, according to the orthodontic bracket 1 in the first exemplary embodiment shown in FIGS. 1-4, the two forces which are exerted on the clip 4 can be reliably cancelled by each other.

Even when the clip 4 is forced to be moved further, after the archwire slot 5 has been opened by moving the clip 4, the inward projections 44a of the clip 4 are retained by the retaining projection 33 of the bracket body 3. Because further movement and deformation of the clip 4 are thus prevented, a breakdown of the clip 4 can be prevented. Moreover, because the lower extended part 42 of the clip 4 is restrained by the retaining parts 93 of the guide groove 9, the clip 4 will not drop from the orthodontic bracket 1. As a result, it is possible to easily handle the orthodontic bracket.

Although a case where the butting wall 91 of the guide groove 9 is positioned below the bottom face 53 of the archwire slot 5 has been described in the first exemplary embodiment shown in FIGS. 1-4, it is also possible to set the position of the butting wall 91 of the guide groove 9, for example, between a position below the first side face 51 of the archwire slot 5 at the curved part side and a position below the side faces 6a of the engaging parts 6 at the opposite side to the curved part 43.

Even in the case where the position of the butting wall 91 is set between the position of the first side face 51 and the position below the side faces 6a, the lower end 45 of the clip 4 is restricted by the butting wall 91 of the guide groove 9 in a closed state of the slot, and the lower end 45 of the clip 4 is positioned between the position below the first side face 51 of the archwire slot 5 at the curved part side and the position below the side faces 6a. Therefore, the lower end 45 of the clip 4 is restrained from interfering with the tooth face, and hence, it is possible to reduce the height of the orthodontic bracket 1.

(Second Exemplary Embodiment)

Figure 5A:
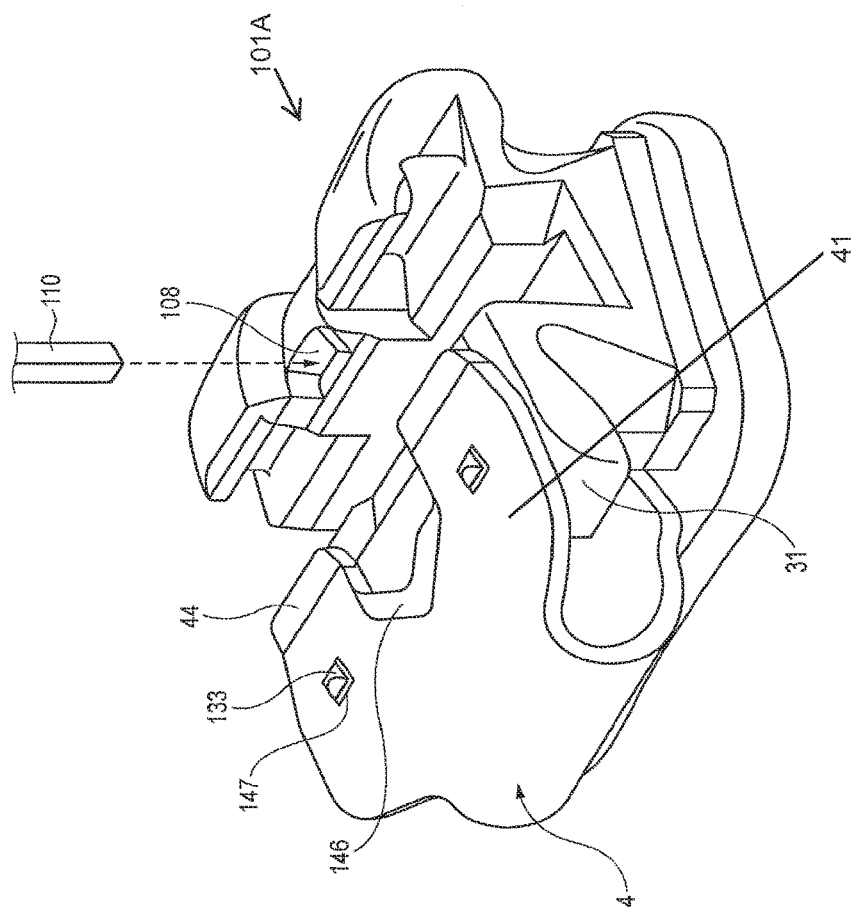
FIG. 5A is a perspective view showing an orthodontic bracket according to a second exemplary embodiment.

In the above described first exemplary embodiment, an example in which the clip 4 is moved by the opening tool 10 in a plate-like shape has been described. However, exemplary embodiments are not limited to the first exemplary embodiment. FIG. 5A is a perspective view showing an orthodontic bracket 101A according to a second exemplary embodiment. The orthodontic bracket 101A is different from the orthodontic bracket 1 in the first exemplary embodiment only in an engaging structure with a tool and a locking structure for retaining a clip. Therefore, in the following description, only the features which are different from the first exemplary embodiment will be described. The same members are denoted with the same reference numerals, and repeated description of the same will be omitted.

There is provided, in the second exemplary embodiment, the orthodontic bracket 101A to which an opening tool 110 in a rod-like shape may be applied. A tool guiding face 108 is formed as a dented part which is slightly larger than the opening tool 110 in the rod-like shape. Moreover, a part between the right and left upper ends 44 of the clip 4 is formed in a V-shape corresponding to a shape of a tip end of the opening tool 110, and a tool locking projection 146 is erected also in a V-shape. Therefore, by inserting the opening tool 110 between the tool guiding face 108 in a dented shape and the tool locking projection 146 in a V-shape, and hooking the opening tool 110 on the tool locking projection 146 thereby to move the clip 4, it is possible to bring the slot into an open state.

In addition, retaining projections 133 are provided on the upper supporting face 31 of the bracket body 3, and right and left engaging holes 147 each in a rectangular shape are formed in the upper extended part 41 of the clip 4. After the clip 4 is moved for the purpose of opening the slot, the retaining projections 133 of the bracket body 3 are engaged with the engaging holes 147 of the clip 4, so that the clip 4 may be prevented from being opened too much.

(First Modification)

Figure 5B:
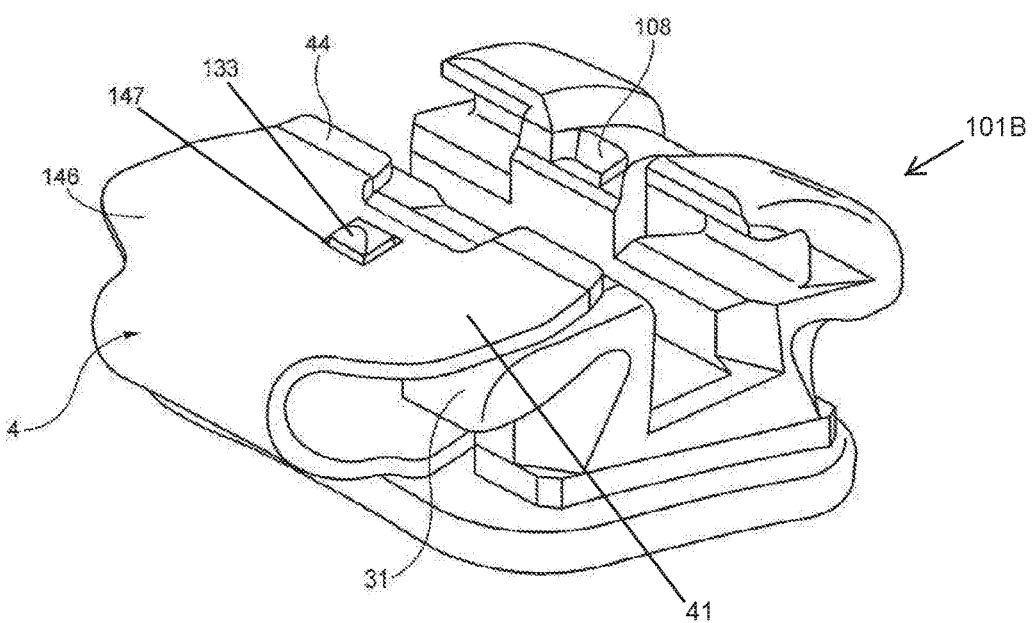
FIGS. 5B and 5C are perspective views showing orthodontic brackets according to a first modification and a second modification, respectively.
Figure 5C:
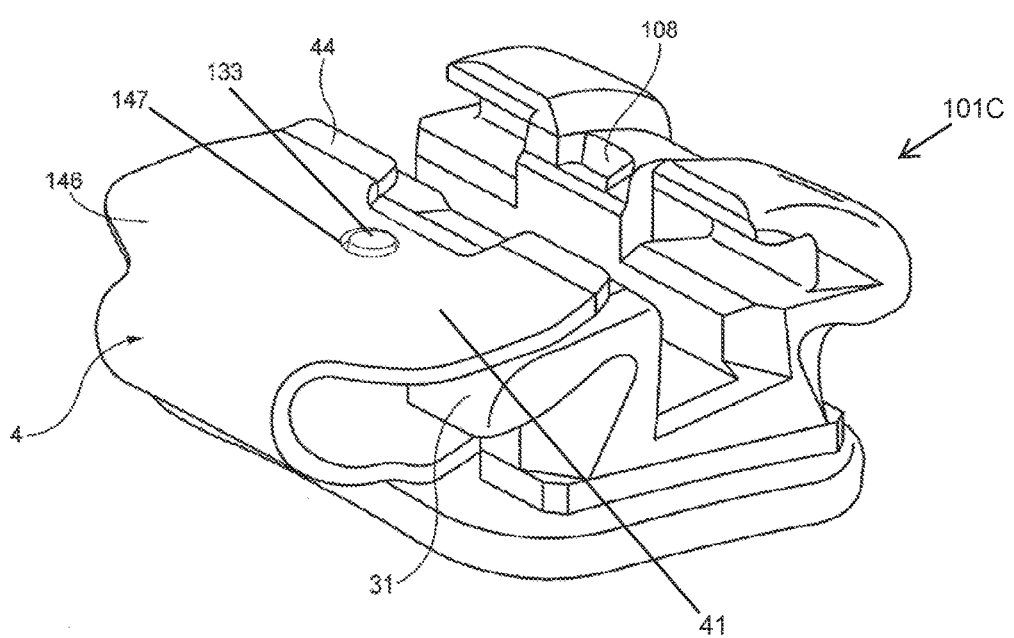

In the above described second exemplary embodiment, an example in which the right and left upper ends 44 of the clip are formed in a V-shape and a tool locking projection 146 is also formed in a V-shape, and a plurality of retaining projections 133 are provided in the upper supporting face of the bracket body 3 is described. However, this is only an example. FIG. 5B shows a perspective view showing an orthodontic bracket 101B according to a first modification of the second exemplary embodiment, and FIG. 5C shows a perspective view showing an orthodontic bracket 101C according to a second modification of the second exemplary embodiment. The orthodontic bracket 101B and the orthodontic bracket 101C are different from the orthodontic bracket 101A in a locking structure for retaining a clip. Therefore, in the following description, only the features which are different from the second exemplary embodiment will be described. The same members are denoted with the same reference numerals, and repeated description of the same will be omitted.

In the orthodontic bracket 101B shown in FIG. 5B, a part between the right and left upper ends 44 of the clip 4 is formed in a straight notch shape rather than a V-shape of the orthodontic bracket 101A. In the orthodontic bracket 101B, only one retaining portion 133 that has a rectangular shape is provided on the upper supporting face 31 of the bracket body 3 in contrast to the orthodontic bracket 101A, and only one engaging hole 147 that corresponds in position to the one retaining portion 133 is formed in the upper extended part 41 of the clip 4 in contrast to the orthodontic bracket 101A.

In the orthodontic bracket 101C shown in FIG. 5C, the one retaining portion 133 has a circular shape rather than a rectangular shape, and similarly the one engaging portion 147 has a corresponding circular shape rather than a corresponding rectangular shape. For example, the one retaining portion 133 may be hemispherical shaped in some exemplary embodiments.

In the second exemplary embodiment, when the clip 4 is moved from a closed position to an open position, the opening tool 110 is inserted in the tool guiding face 108 that is formed as a dented part provided at the center in the longitudinal direction of the engaging part 6. By contrast, in the first and second modifications shown in FIGS. 5B and 5C, the clip 4 is opened by inserting the opening tool 110 into the one engaging hole 147.

In the related art, there are provided clips having holes for using a tool to open the clip. For example, U.S. Pat. No. 5,906,486 shows such an example. However, in these cases in the related art, there is a disadvantage in that overstress is easily applied to the clip by the tool and thus the clip is opened too much and deformed. To address this disadvantage, a tool and bracket specifically designed to suppress the movable area of the tool with respect to the bracket has been proposed. Examples of such specially designed tools and brackets are shown in U.S. Pat. Nos. 6,368,105 and 7,993,132. However, in the case of these specially designed tools and brackets, there is disadvantage in that a dedicated tool is then required, and a probe which is generally used by a doctor cannot be used. In other words, the doctor is required to purchase a special tool for each specially designed tool and bracket.

The first and second modifications address all these disadvantages by providing the one retaining portion 133 and the one engaging hole 147. The one retaining portion 133 and the one engaging hole 147 make a unique operation of the orthodontic bracket 1 that addresses the disadvantages possible. In operation, the clip 4 is opened by inserting the tip end of an opening tool 110 into the one engaging hole 147 and using the opening tool 110 to move the clip 4 from the closed position to the open position. When the clip 4 reaches the open position, the one retaining portion 133 engages with the one engaging hole 147 thus pushing the tip end of the opening tool 110 out from the one engaging hole 147 by the one retaining portion 133 at the same time or before the one retaining projection 133 is engaged with the one engaging hole 147 to hold the clip 4 in the open position. Therefore, overstress is prevented from being applied to the clip 4 and the clip 4 is prevented from being opened too much and deformed as in the related art.

(Third Exemplary Embodiment)

In the above described first and second exemplary embodiments, an example where the upper ends 44 of the clip 4 having a bifurcated shape are inserted into the engaging parts 6 thereby to close the archwire slot 5 has been described. However, exemplary embodiments are not limited to this structure. An orthodontic bracket 201 in a third exemplary embodiment will be described, referring to FIGS. 6 and 7.

The orthodontic bracket 201 in the third exemplary embodiment is different from the orthodontic bracket 1 in the first exemplary embodiment only in that the clip and a part of the bracket body surrounding the engaging part have different shapes. Therefore, in the following description, only the features which are different from the first exemplary embodiment will be described. The same members are denoted with the same reference numerals, and description of the same will be omitted.

Figure 6:
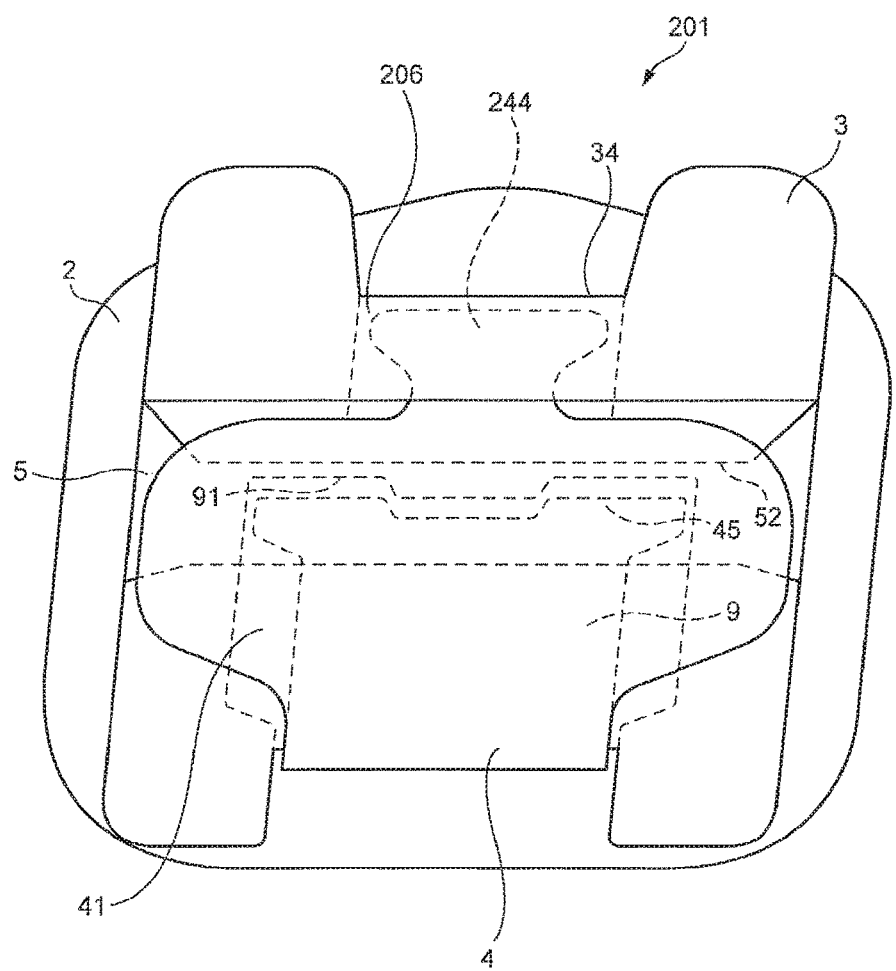
FIG. 6 is a plan view of an orthodontic bracket according to a third exemplary embodiment in a closed state of a slot.
Figure 7:
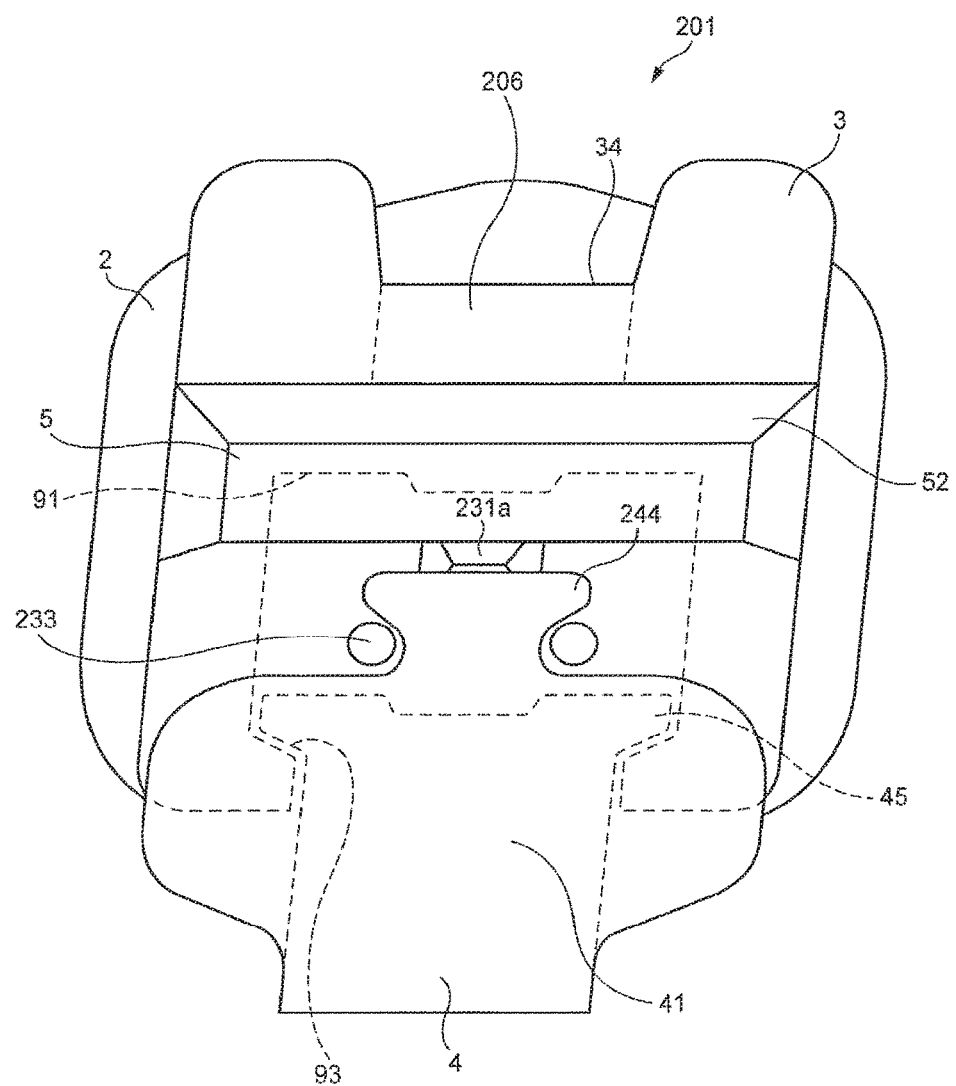
FIG. 7 is a plan view of the orthodontic bracket according to the third exemplary embodiment in an opened state of the slot.

FIG. 6 is a plan view of the orthodontic bracket 201 in a closed state of the slot, and FIG. 7 is a plan view of the orthodontic bracket 201 in an open state of the slot. In the third exemplary embodiment, the upper extended part 41 of the clip 4 is provided with an upper end 244 which is projected from a center position in a lateral direction thereof. The second side face 52 at the opposite side to the curved part of the archwire slot 5 is provided with an insertion hole 206 into which the upper end 244 of the clip 4 can be inserted. The insertion hole 206 is so formed as to pass through the bracket body 3 from the second side face 52 at the opposite side of the archwire slot 5 from the curved part 43 up to the end face 34 at the opposite side of the bracket body 3 to the curved part 43.

In the closed state of the slot, as shown in FIG. 6, the upper end 244 of the clip 4 is inserted into the insertion hole 206. On this occasion, even though an upward force is exerted on the archwire, and the upper extended part 41 of the clip 4 tends to be lifted upward, an upper face of the insertion hole 206 is butted against the upper end 244 of the clip 4 thereby to prevent withdrawal of the clip 4.

As shown in FIG. 7, in the open state of the slot, excessive opening preventing projections 233 which are provided on the upper supporting face 31 of the bracket body 3 intrude into dented parts which are provided at both sides of a connecting part between the upper end 244 and the upper extended part 41 of the clip 4. In this manner, the clip 4 is prevented from moving too much. Moreover, an overriding step 231a is provided on the upper supporting face 31 of the bracket body 3 at its end close to the archwire slot 5. The open state of the slot is maintained, by butting this overriding step 231a against the upper end 244 of the clip 4.

In the third exemplary embodiment, in the closed state of the slot, the lower end 45 of the clip 4 does not pass through the bracket body 3 up to the end face 34 at the opposite side from the curved part, and the guide groove 9 is positioned below the archwire slot 5, in the same manner as in the above described first and second exemplary embodiments. Therefore, in the third exemplary embodiment, it is possible to provide the orthodontic bracket 201 having a lower height, and having less possibility that the clip may be detached.

Figure 8:
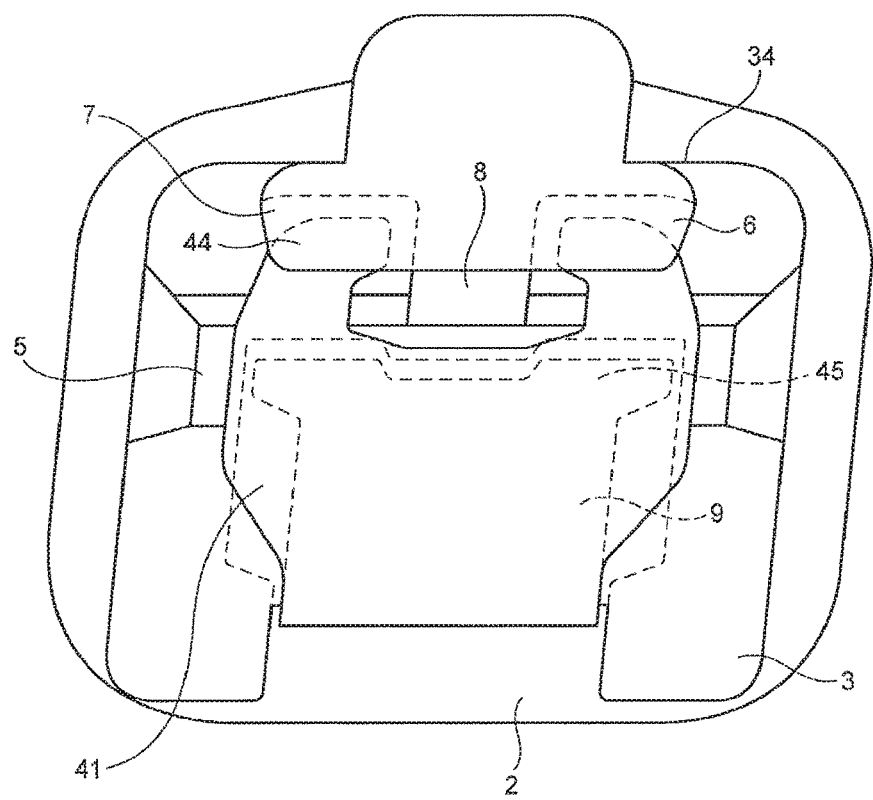
FIG. 8 is a plan view of an orthodontic bracket according to a third modification.

In the above described first to third exemplary embodiments, the orthodontic brackets 1, 101, 201 of a twin bracket type having two pairs of the wings which are provided in parallel with the bracket body 3 have been described by way of examples. However, exemplary embodiments are not limited to the orthodontic bracket of the twin bracket type. FIG. 8 is a plan view of an orthodontic bracket according to a third modification. It is also possible to apply the inventive concept to a single bracket having a single wing, as shown in FIG. 8.

Figure 9:
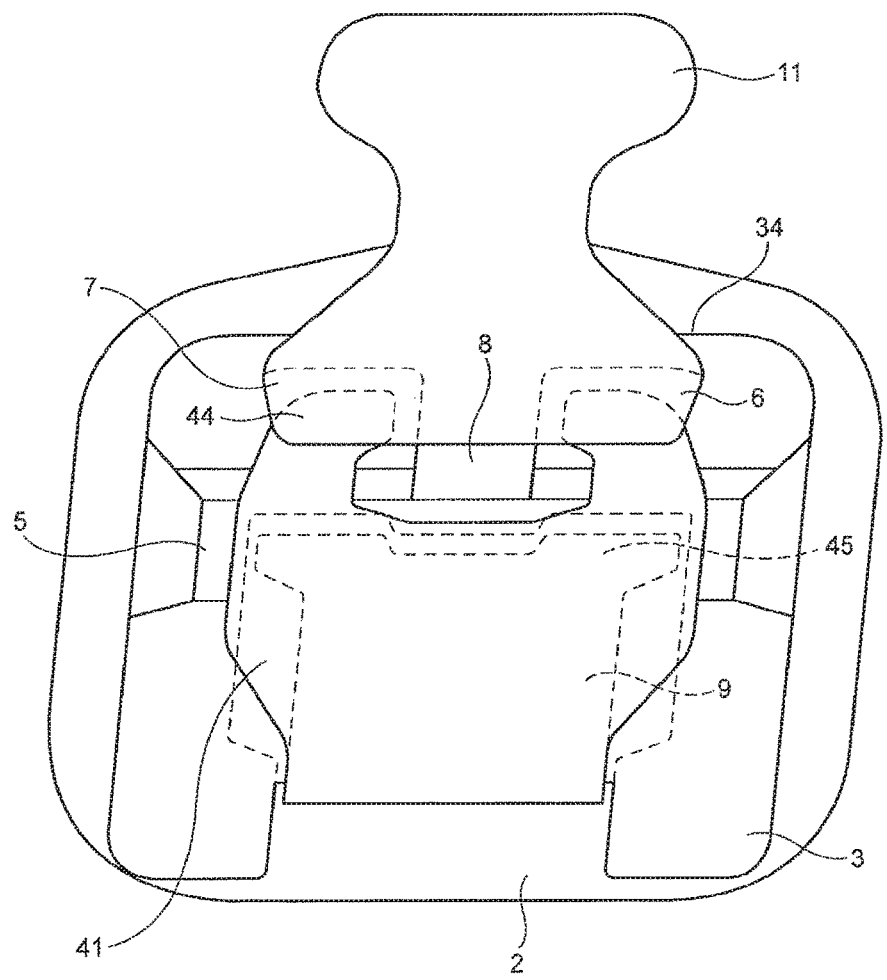
FIG. 9 is a plan view of an orthodontic bracket according to a fourth modification.

FIG. 9 is also a plan view of an orthodontic bracket according to a fourth modification which is different from the third modification as shown in FIG. 8. As shown in FIG. 9, a hook 11 for hooking an elastic band for drawing may be provided on the bracket body 3. By employing such a structure, it is possible to apply the inventive concept to the orthodontic bracket which may be used with an orthodontic treatment for correcting dentition by hooking the elastic band. Although a case where the orthodontic bracket of the single bracket type is provided with the hook 11 is shown in FIG. 9, as an example, it is also possible to provide the hook 11 on the orthodontic brackets 1, 10 1, 201 of the twin bracket type in the first to third exemplary embodiments.

Also in the third and fourth modifications as shown in FIGS. 8 and 9, in the closed state of the slot, the lower end 45 of the clip 4 does not pass through the bracket body 3 up to the end face 34 at the opposite side to the curved part, and the guide groove 9 is positioned below the archwire slot 5, in the same manner as in the above described first and second exemplary embodiments. Therefore, in the third and fourth modifications, it is possible to provide the orthodontic bracket 201 having a lower height, and having less possibility that the clip may be detached.

According to the above-described exemplary embodiments and modifications, an orthodontic bracket may be provided that comprises a base part in a plate-like shape which is directly or indirectly fixed to a tooth at its bottom face; a bracket body which is fixed to an upper face of the base part; and a clip having a substantially U-shape in section which is mounted on the bracket body so as to move, and includes an upper extended part extending along an upper face of the bracket body, a lower extended part extending along a lower face of the bracket body, and a curved part interconnecting the upper and lower extended parts, wherein an archwire slot in a shape of a groove capable of containing an archwire is provided on the upper face of the bracket body so as to extend in a direction perpendicular to a moving direction of the clip, an engaging part into which an end of the upper extended part of the clip can be inserted is provided on a side face at an opposite side to the curved part of the archwire slot, a guide groove for guiding the lower extended part in the moving direction of the clip is provided on the lower face of the bracket body, the guide groove being provided below the archwire slot, and in a state where the end of the upper extended part of the clip is inserted into the engaging part, an end of the lower extended part of the clip does not pass through the bracket body up to an end face at the opposite side to the curved part of the bracket body.

The guide groove may have a flat face part which is positioned below the archwire slot substantially in parallel with a bottom face of the archwire slot.

A wire retaining hood part which protrudes toward the curved part may be provided above the engaging part, and a protruding end of the wire retaining hood part may be positioned more remote from the curved part than the side face at the opposite side to the curved part of the archwire slot.

The end of the lower extended part of the clip may be provided with an enlarged width part, and the guide groove may be provided with a clip retaining part at the curved part side of the guide groove, the clip retaining part having a smaller distance therebetween than a width of the enlarged width part of the clip.

An excessive opening preventing part may be provided on the upper extended part of the clip, and an excessive opening preventing projection to be engaged with the excessive opening preventing part may be provided on the upper face of the bracket body at the curved part side.

Ends in a lateral direction of the upper extended part of the clip may be projected in a bifurcated shape, the engaging part may be provided on the archwire slot as engaging parts so as to correspond to the ends of the upper extended part which are projected in the bifurcated shape, a tool guiding face which is in flush with the side face at the opposite side to the curved part of the archwire slot may be provided between the engaging parts, and an upper part of the tool guiding face may have a taper shape which is open upward.

The ends in a lateral direction of the upper extended part of the clip may be projected in a bifurcated shape, and a tool locking projection which projects upward may be provided at a center in a lateral direction between the ends of the upper extended part in the bifurcated shape.

A butting wall against which the end of the lower extended part of the clip is butted may be provided at the opposite side to the curved part of the guide groove, and the butting wall may be provided with a through hole for removing foreign bodies which communicates the guide groove to the exterior.

According to the orthodontic bracket as in the various exemplary embodiments and modifications described above, in a state where the end of the upper extended part of the clip is inserted into the engaging part, the lower extend part of the clip is set to be shorter so that the end of the lower extended part may not pass through the bracket body up to the end face at the opposite side to the curved part. Therefore, in the closed state of the slot where the end of the upper extended part is inserted into the engaging part, the lower extended part of the clip does not interfere with the tooth face, and the thickness of the bracket body can be reduced. As a result, it is possible to reduce the height of the bracket.

Moreover, in case where the archwire tends to lift the upper extended part of the clip, the lower extended part of the clip comes into contact with the guide groove thereby to create a repulsive force against the lifting force. On this occasion, two forces are cancelled by each other, because the guide groove is provided below the archwire slot, and a rotation moment will not be exerted on the clip. Therefore, the clip will not be rotated, and there is no such anxiety that the clip may be opened. As a result, it is possible to provide the orthodontic bracket which has lower height, and has less possibility that the slot may be unintentionally opened.

The foregoing exemplary embodiments, modifications, and advantages are merely examples and are not to be construed as limiting the present disclosure. The description of the exemplary embodiments is intended to be illustrative, and not to limit the scope of the inventive concept, as defined by the appended claims, and many alternatives, modifications, and variations will be apparent to those skilled in the art.

What is claimed is:

1. An orthodontic bracket comprising:
   a base part;
   a bracket body mounted on the base part;
   a clip having a U-shaped cross-section, the clip being mounted on the bracket body and comprising an upper part along an upper face of the bracket body, a lower part along a lower face of the bracket body, and a curved part therebetween;
   an archwire slot in the upper face of the bracket body that extends perpendicular to a moving direction of the clip;
   an engaging part for receiving a first end of the clip provided on a side face of the archwire slot opposite to the curved part;
   a guide groove for guiding the lower part of the clip in the moving direction of the clip is provided on the lower face under the archwire slot;
   a tool guiding face provided at a center of the engaging part in a longitudinal direction of the engaging part; and
   a space for receiving a tool for opening the clip provided adjacent to the tool guiding face,
   wherein, in a state of insertion, the lower part is below a bottom face of the archwire slot and a second end of the clip does not pass through an end face of the bracket body at an opposite side from the curved part,
   wherein a lower extended part of the clip does not extend past the archwire slot in a locked position in which the first end is received into the engaging part, and
   wherein the guide groove is provided underneath the archwire slot such that the guide groove is positioned on a hypothetical line drawn perpendicular to a bottom portion of the archwire slot and passing through the bottom portion of the archwire slot.

2. The orthodontic bracket of claim 1, wherein:
   the bracket body comprises a retaining projection provided on an upper face thereof; and
   the clip comprises an engaging hole provided in the upper part of the clip in a position that corresponds to a position of the retaining projection of the bracket body such that the retaining projection projects through the engaging hole when the clip is in an open position thereon.

3. The orthodontic bracket of claim 2, wherein the retaining projection is rectangular shaped, and the engaging hole is rectangular shaped.

4. The orthodontic bracket of claim 2, wherein the retaining projection is circular shaped, and the engaging hole is circular shaped.

5. The orthodontic bracket of claim 2, wherein the retaining projection is hemispherical shaped, and the engaging hole is circular shaped.

6. An orthodontic bracket comprising:
   a base part;
   a bracket body mounted on the base part;
   a clip having a U-shaped cross-section, the clip being mounted on the bracket body and comprising an upper part along an upper face of the bracket body, a lower part along a lower face of the bracket body, and a curved part therebetween;
   an archwire slot in the upper face of the bracket body that extends perpendicular to a moving direction of the clip;
   an engaging part for receiving a first end of the clip provided on a side face of the archwire slot opposite to the curved part;
   a guide groove for guiding the lower part of the clip in the moving direction of the clip is provided on the lower face under the archwire slot;
   a tool guiding face provided at a center of the engaging part in a longitudinal direction of the engaging part; and
   a space for receiving a tool for opening the clip provided adjacent to the tool guiding face,
   wherein, in a state of insertion, the lower part is below a bottom face of the archwire slot and a second end of the clip does not pass through an end face of the bracket body at an opposite side from the curved part,
   wherein a lower extended part of the clip does not extend past the archwire slot in a locked position in which the first end is received into the engaging part,
   wherein the guide groove is provided underneath the archwire slot such that the guide groove is positioned on a hypothetical line drawn perpendicular to a bottom portion of the archwire slot and passing through the bottom portion of the archwire slot,
   wherein the second end of the clip is provided with an enlarged width part, and the guide groove is provided, at a side of the curved part, with clip retaining parts that protrude inward from sides of the guide groove such that a distance between the clip retaining parts is smaller than a width of the enlarged width part of the clip.

* * * * *